US012128077B2

(12) United States Patent
Vedel et al.

(10) Patent No.: US 12,128,077 B2
(45) Date of Patent: Oct. 29, 2024

(54) STRAINS, COMPOSITION AND METHOD OF USE

(71) Applicant: Lactobio A/S, Copenhagen O (DK)

(72) Inventors: Charlotte Vedel, Copenhagen O (DK); Ida Blomquist Jorgensen, Copenhagen (DK); Soren Kjaerulff, Copenhagen (DK)

(73) Assignee: L'Oreal S.A., Paris (FR)

( * ) Notice: Subject to any disclaimer, the term of this patent is extended or adjusted under 35 U.S.C. 154(b) by 263 days.

(21) Appl. No.: 17/417,654

(22) PCT Filed: Aug. 8, 2019

(86) PCT No.: PCT/EP2019/071348
§ 371 (c)(1),
(2) Date: Jun. 23, 2021

(87) PCT Pub. No.: WO2020/098988
PCT Pub. Date: May 22, 2020

(65) Prior Publication Data
US 2022/0110986 A1   Apr. 14, 2022

(30) Foreign Application Priority Data

Jan. 4, 2019  (DK) .......................... PA 2019 00009
Apr. 17, 2019 (DK) .......................... PA 2019 00469

(51) Int. Cl.
*A61K 39/02*   (2006.01)
*A61K 35/747*  (2015.01)
*A61P 31/04*   (2006.01)
*C12N 1/20*    (2006.01)
*C12R 1/225*   (2006.01)

(52) U.S. Cl.
CPC ............ *A61K 35/747* (2013.01); *A61P 31/04* (2018.01); *C12N 1/205* (2021.05); *C12R 2001/225* (2021.05)

(58) Field of Classification Search
None
See application file for complete search history.

(56) References Cited

U.S. PATENT DOCUMENTS

| 5,032,399 | A  |  7/1991 | Gorbach et al. |
| 2014/0186409 | A1 |  7/2014 | Lang et al. |
| 2015/0366920 | A1 | 12/2015 | Desroche et al. |
| 2017/0224750 | A1* | 8/2017 | Callanan ............. A61K 36/61 |
| 2017/0281695 | A1 | 10/2017 | Gantz et al. |
| 2018/0036356 | A1* | 2/2018 | Desroche ............ A61K 35/741 |

FOREIGN PATENT DOCUMENTS

| AU | 719544 B2 | 5/2000 |
| EP | 2364712 A1 | 9/2011 |
| EP | 2704704 A1 | 3/2014 |
| EP | 2823822 A1 | 1/2015 |
| FI | 92498 B | 8/1994 |
| KR | 2012 0038698 A | 4/2012 |
| WO | 2006013441 A2 | 2/2006 |
| WO | 2006013441 A3 | 2/2006 |
| WO | WO 2010/130662 A1 | 11/2010 |
| WO | WO 12/152270 A1 | 11/2012 |
| WO | WO 12/156491 A1 | 11/2012 |
| WO | 2014096641 A1 | 6/2014 |
| WO | WO2016023688 A1 * | 2/2016 |
| WO | WO 2017/060468 A1 | 4/2017 |
| WO | WO 2017/220525 A1 | 12/2017 |

OTHER PUBLICATIONS

Huang et al (Microorganisms. Aug. 2021; 9(8): 1570. pp. 1-12).*
Wertheim, et al., "The Role of Nasal Carriage in *Staphylococcus aureus* Infections," *Lancet Infect. Dis.* 5(12): 751-762 (2005). <https://www.cdc.gov/nchs/icd/icd9.htm>.
Leung & Soter, "Cellular and Immunologic Mechanisms in Atopic Dermatitis," *J. Am. Acad. Dermatol.* 44(1); S1-S12 (2001).
Nutten, "Atopic Dermatitis: Global Epidemiology and Risk Factors," *Ann. Nutrit. Metabol.* 66(1); 8-16 (2015).
Totté, et al., "A Systematic Review and Meta-analysis on *Staphylococcus aureus* Carriage in Psoriasis, Acne and Rosacea," *Eur J Clin Microbiol Infect Dis* 35:1069-1077 (2016).
Silverberg, "Public Health Burden and Epidemiology of Atopic Dermatitis," *Dermatologic Clinics* 35(3); 283-289 (2017).
McPherson, "Current Understanding in Pathogenesis of Atopic Dermatitis," *Indian J. Dermatol.* 61(6): 649-655 (2016).
Ring, et al., "Guidelines for Treatment of Atopic Eczema (Atopic Dermatitis) Part I," *J. Eur. Acad. Dermatol. Venereoi* 26:1045-1060 (2012).
Wollenberg, et al., "Conjunctivitis Occurring in Atopic Dermatitis Patients Treated with Dupilumabeclinical Characteristics and Treatment," *J. Allergy Clin. Immunol: In Practice*, 6(5): 1778-1780 (2018).
Dobie & Gray, "Fusidic Acid Resistance in *Staphylococcus aureus*," *Arch Dis Child* 89:74-77 (2004).
Barrett, et al., "Methicillin-Resistant *Staphylococcus aureus* at Boston City Hospital* Bacteriologic and Epidemiologic Observations," *New England J Med.* 279: 441-448 (1968).

(Continued)

*Primary Examiner* — Jennifer E Graser
(74) *Attorney, Agent, or Firm* — Honigman LLP

(57) ABSTRACT

The present invention relates to a bacterial strain having a genetic homology of at least 95% to one or more of the bacterial strains selected from the group consisting of:
  *Weissella viridescens* LB10G, which is deposited as DSM 32906;
  *Lactobacillus paracasei* LB113R, which is deposited as DSM 32907;
  *Lactobacillus plantarum* LB244R, which is deposited as DSM 32996;
  *Lactobacillus paracasei* LB116R, which is deposited as DSM 32908;
  *Enterococcus faecium* LB276R, which is deposited as DSM 32997;
  *Lactobacillus plantarum* LB316R, which is deposited as DSM 33091;
  *Leuconostoc mesenteriodes* LB341R;
  *Leuconostoc mesenteriodes* LB349R, which is deposited as DSM 33093;
  *Lactobacillus plantarum* LB356R, which is deposited as DSM 33094;
  *Lactobacillus plantarum* LB312R, which is deposited as DSM 33098.

15 Claims, No Drawings

(56) References Cited

OTHER PUBLICATIONS

Jevons, "'Celbenin'-resistant Staphylococci," *British Med. J.* 1(5219):124-125 (1961).
<https://www.cdc.gov/mrsa/tracking/index.html>, Feb. 1, 2019.
Dantes, et al., "National Burden of Invasive Methicillin-Resistant *Staphylococcus aureus* Infections, United States, 2011," *JAMA Int. Med.* 173(21): 1970-1978 (2013).
Defres, et al., "MRSA as a Cause of Lung Infection Including Airway Infection, Community Acquired Pneumonia and Hospital-acquired Pneumonia," *Eur. Resp. J.* 34(6): 1470-1476 (2009).
García-Álvarez, et al. "Meticillin-resistant *Staphylococcus aureus* with a Novel mecA Homologue in Human and Bovine Populations in the UK and Denmark: A Descriptive Study," *Lancet Infect. Dis.* 11(8): 595-603 (2011).
Shore, et al., "Detection of Staphylococcal Cassette Chromosome mec Type XI Carrying Highly Divergent *mecA, mecI, mecR1, blaZ,* and *ccr* Genes in Human Clinical Isolates of Clonal Complex 130 Methicillin-Resistant *Staphylococcus aureus,*" *Antimicrob. Agents Chemo.* 55(8): 3765-3773 (2011).
De Boer, et al., "Prevalence of Methicillin-resistant *Staphylococcus aureus* in Meat," *Int. J. Food Microbiol.* 134(1-2): 52-56 (2009).
Köck, et al., "Methicillin-resistant *Staphylococcus aureus* (MRSA): Burden of Disease and Control Challenges in Europe," *Eurosurveillance* 15(41): 19688 (2010).
Shigemura, et al., "Pathogen Occurrence and Antimicrobial Susceptibility of Urinary Tract Infection Cases During a 20-Year Period (1983-2002) at a Single Institution in Japan," *Japan. J. Infect. Dis.* 58(5): 303-308 (2005).
Conway, et al., "Survival of Lactic Acid Bacteria in the Human Stomach and Adhesion to Intestinal Cells," *J. Dairy Sci.* 70:1-12 (1987).
Goldin, et al. "Survival of *Lactobacillus* Species (Strain GG) in Human Gastrointestinal Tract," *Dig. Dis. Sci.* 37:121-128 (1992).
Kleeman and Klaenhammer, "Adherence of *Lactobacillus* Species to Human Fetal Intestinal Cells," *J. Dairy Sci.*65:2063-2069 (1982).
Castagliuolo, et al., "*Saccharomyces boulardii* Protease Inhibits *Clostridium difficile* Toxin A Effects in the Rat Ileum," *Infect. Immun.* 64:5225-5232 (1996).
Castagliuolo, et al., "*Saccharomyces boulardii* Protease Inhibits the Effects of *Clostridium difficile* Toxins A and B in Human Colonic Mucosa," *Infect. Immun.* 67:302-307 (1999).
Pothoulakis, et al., "*Saccharomyces boulardii* Inhibits Clostridium difficile Toxin A Binding and Enterotoxicity in Rat Ileum," *Gastroenterology* 104:1108-1115 (1993).
Fukushima, et al. "Effect of a Probiotic Formula on Intestinal Immunoglobulin A Production in Healthy Children," *Int. J. Food Microbiol.* 42:39-44 (1998).
Malin, et al., "Promotion of IgA Immune Response in Patients with Crohn's Disease by Oral Bacteriotherapy with *Lactobacillus* GG," *Ann. Nutr. Metab.* 40:137-145 (1996).
Dowarah, et al., "Selection and Characterization of Probiotic Lactic Acid Bacteria and its Impact on Growth, Nutrient Digestibility, Health and Antioxidant Status in Weaned Piglets," *PLoS ONE,* 13(3) (2018).
Khare & Tavazoie, "Multifactorial Competition and Resistance in a Two-Species Bacterial System," *PLoS Genetics,* 11(12): 1-21 (2015).
Clausen, et al., "*Staphylococcus aureus* Colonization in Atopic Eczema and its Association with Filaggrin Gene Mutations," *Br. J. Dermatol.* 177: 1394-1400 (2017).
Cisar, et al. "Specificity of Coaggregation Reactions Between Human Oral Streptococci and Strains of Actinomyces Viscosus or Actinomyces Naeslundii" Infection and Immunity 24 (3): 742-52 (1979).
Zhang, et al., "Interstrain Interactions Between Bacteria Isolated from Vacuum-packaged Refrigerated Beef," *Appl Environ Microbiol* 81:2753-2761 (2015).
Arena, et al., "Use of Lactobacillus Plantarum Strains as a Bio-Control Strategy Against Food-Borne Pathogenic Microorganisms," *Frontiers in Microbiology* 7 (Apr): 1-10 (2016).
Wong, et al., "Inhibition of *Staphylococcus aureus* by Crude and Fractionated Extract from Lactic Acid Bacteria", *Beneficial Microbes,* 6(1): 129-139 (2015).
Soleimani, et al., "Antagonistic Activity of Probiotic Lactobacilli Against *Staphylococcus aureus* Isolated from Bovine Mastitis," *African Journal of Microbiology Research* 4(20): 2163-2173 (2010).
Sica, et al., "Isolation, Identification and Antimicrobial Activity of Lactic and Acid Bacteria from the Bahía Blanca Estuary," *Revista de Biología Marina y Oceanografía,* 45(3); 389-397 (2010).
Search Report from Danish Application No. PA 2019 00009; Dated: Jun. 16, 2019.
Mottin, Vitória H. M. and Edna Sayuri Suyenaga. "An approach on the potential use of probiotics in the treatment of skin conditions: acne and atopic dermatitis." International Journal of Dermatology 57 (2018): n. pag.

\* cited by examiner

STRAINS, COMPOSITION AND METHOD OF USE

RELATED APPLICATIONS

This application is a national stage filing under 35 U.S.C. 371 of International Application No. PCT/EP2019/071348, filed Aug. 8, 2019, which claims priority to Denmark Application No. PA 2019 00009, filed Jan. 4, 2019, and Denmark Application No. PA 2019 00469, filed Apr. 17, 2019. The entire teachings of said applications are incorporated by reference herein. International Application PCT/EP2019/071348 was published under PCT Article 21(2) in English.

TECHNICAL FIELD OF THE INVENTION

The present invention relates to novel bacterial stains. In particular, the present invention relates to novel bacterial strains for use in for use in treating; alleviating, suppressing; prophylaxis; and/or preventing growth of a pathogenic micro-organism.

Background of the Invention

The Gram-positive bacterium, *Staphylococcus aureus*, is one of the most frequently encountered human pathogens. It is particularly common in the human nasal passages, where it is found either intermittently or permanently in about 50% of the human population. Even though colonization with *S. aureus* is, in most cases, non-symptomatic, the pathogen can cause infections when the skin's protective barrier function is breached. *Staphylococcus* infections are thus often associated with skin diseases as dermatitis, eczema, carbuncle, cellulitis, rosacea, psoriasis, diaper rash, impetigo and wounds.

As an example of skin infections is atopic dermatitis, which is a chronic or chronically relapsing inflammatory skin disease arising from a complex interrelationship of environmental, immunologic, genetic, and pharmacologic factors.

All of these genetic and environmental factors contribute to the following characteristic features.
1: An abnormal microbial colonization with pathogenic organisms such as *Staphylococcus aureus* (compared with *Staphylococcus epidermidis* in normal individuals), which subsequently increases the patients' susceptibility to skin infection; additionally, *S. aureus* produces enterotoxin, inducing the production of enterotoxin-specific IgE, which results in more T cell recruitment;
2: The involvement in the initiation phase of the disease, which consequently increases immunoglobulin E (IgE) production;
3: Skin barrier dysfunction or dry skin due to abnormal lipid metabolism and/or epidermal structural protein formation; and
4: A psychosomatic influence in sufferers due to the imbalance in the autonomic nervous system, with subsequent increased production of mediators from various inflammatory cell.

Atopic dermatitis is typically treated by topical moisturizers/emollients or corticosteroids being selected as a first line of therapy, followed by topical calcineurin inhibitors as a second line for patients who are not controlled on first-line treatments.

Currently, there are no topical treatments for mild-to-moderate atopic dermatitis patients that come without significant side effects like local thinning of the skin at the application site; exacerbation or risk of acne in patients and burning sensation.

The unmet needs for atopic dermatitis patients still persist. Topical treatments still cause patients to suffer as a result of well-known side effects as pruritus. Scratching simply worsens disease symptoms, leading to lichenification, excoriation, and a breakdown of the skin barrier, creating a vicious cycle for disease sufferers and increasing the risk of skin infections.

The most difficult unmet need that has yet to be addressed is preventing and treatment of skin infections by *Staphylococcus aureus*, in particular *Staphylococcus* resistant to antibiotics an avoiding additional antibiotic resistance.

Even many different pathogen microorganisms have been found and may embrace bacterial microorganisms; viral microorganisms; fungal microorganisms; parasite microorganisms; and algal microorganisms, the Gram-positive bacterium, *Staphylococcus aureus*, is one of the most frequently encountered human pathogens.

With the discovery of penicillin in 1928, and its mass production in the early 1940s, infections with *S. aureus* were mostly treatable, without any major complications. However, clinicians soon observed the emergence of penicillin-resistant strains of *S. aureus*, which was largely due to bacterial expression of beta-lactamases, enzymes that disrupt the beta-lactam ring structure in the penicillin and cephalosporin classes of antibiotics (beta-lactam antibiotics), destroying their antimicrobial activity. Methicillin, a novel penicillin analogue that was resistant to beta-lactamases, was introduced in 1959, and was initially effective against penicillin-resistant *S. aureus* strains. However, this success was short-lived, as the first methicillin-resistant *S. aureus* (MRSA) strain had been identified in the laboratory by 1961, and cases of MRSA were first observed in the clinic in 1968.

MRSA infections have occurred predominantly in the hospital setting, and MRSA is currently one of the most common nosocomial pathogens, and thus a leading cause of a variety of hospital-acquired infections (HAIs). Since the 1990s, a new type of MRSA, known as community-associated MRSA (CA-MRSA), has emerged. CA-MRSA can not only be distinguished genetically from healthcare-associated MRSA (HA-MRSA) strains, but also exhibits different virulence and antibiotic resistance patterns. Recently, crossing of different CA-MRSA and HA-MRSA strains has been observed, which often makes it difficult to determine the origin of the infecting MRSA strain.

HA-MRSA infections is associated with major clinical complications, and occurs frequently in patients on ventilators, and in those who had surgical site wounds or surgical implants or required surgical wound drainage. Moreover, HA-MRSA infections frequently leads to nosocomial pneumonia or bacteremia, which are associated with high morbidity and mortality.

Since *S. aureus* are not only infects humans, but also other mammals, infected livestock and pets have been an additional origin of transmission. Livestock-associated MRSA (LA-MRSA) has been identified, mostly in pig populations, with colonization rates varying drastically, from 10-80%, but LA-MRSA has also found in ruminants and poultry.

LA-MRSA is an increasing problem for the livestock industry. Subjects like stables, stalls, animals, farmers, farmers household members, personal and visitors of stables as well as slaughter houses and animal transport vehicles get contaminated with LA-MRSA. These subjects can carry the LA-MRSA and be the reason for the LA-MRSA to be transferred between subjects and thus spreading the LA-MRSA among healthy carriers, also with a further risk of spreading the MRSA through carriers into hospitals or nursery homes as well as to patients with inflammatory skin diseases as eczema and atopic dermatitis, carbuncle, cellulitis, rosacea, psoriasis, wound and burns or to humans including children and infants resulting in diaper rash and impetigo caused by MRSA.

Hence, an improved treatment of pathogenic microorganism, like MRSA, would be advantageous, and in particular a more efficient and/or reliable treatment of pathogenic microorganism, like MRSA without the disadvantages of the presently available treatments, like inflammatory skin diseases as eczema and atopic dermatitis, carbuncle, cellulitis, rosacea, psoriasis, wound and burns or to humans including children and infants resulting in diaper rash and impetigo; and without inducing further resistance, e.g. antibiotic resistance in the pathogenic microorganism would be advantageous.

SUMMARY OF THE INVENTION

Thus, an object of the present invention relates to a microorganism, a composition and a method for treating a pathogenic bacterial infection in a subject, such as in a mammal.

In particular, it is an object of the present invention to provide a microorganism, a composition and a method for treating a pathogenic bacterial infection in a subject, such as in a mammal, which solves the above-mentioned problems of the prior art with skin infections, skin diseases, morbidity; mortality caused by infection and antibiotic resistance. Thus, one aspect of the invention relates to a bacterial strain having a genetic homology of at least 95% to one or more of the bacterial strains selected from the group consisting of:
  *Weissella viridescens* LB10G, which is deposited as DSM 32906;
  *Lactobacillus paracasei* LB113R, which is deposited as DSM 32907;
  *Lactobacillus plantarum* LB244R, which is deposited as DSM 32996;
  *Lactobacillus paracasei* LB116R, which is deposited as DSM 32908;
  *Enterococcus faecium* LB276R, which is deposited as DSM 32997;
  *Lactobacillus plantarum* LB316R, which is deposited as DSM 33091;
  *Leuconostoc* mesenteriodes LB341R;
  *Leuconostoc* mesenteriodes LB349R, which is deposited as DSM 33093;
  *Lactobacillus plantarum* LB356R, which is deposited as DSM 33094;
  *Lactobacillus plantarum* LB312R, which is deposited as DSM 33098;

Thus, another aspect of the invention relates to a bacterial strain having a genetic homology of at least 95% to one or more of the bacterial strains selected from the group consisting of:
  *Weissella viridescens* LB10G, which is deposited as DSM 32906;
  *Lactobacillus paracasei* LB113R, which is deposited as DSM 32907;
  *Lactobacillus plantarum* LB244R, which is deposited as DSM 32996;
  *Lactobacillus paracasei* LB116R, which is deposited as DSM 32908;
  *Enterococcus faecium* LB276R, which is deposited as DSM 32997;
  *Lactobacillus plantarum* LB316R, which is deposited as DSM 33091;
  *Leuconostoc* mesenteriodes LB349R, which is deposited as DSM 33093;
  *Lactobacillus plantarum* LB356R, which is deposited as DSM 33094;
  *Lactobacillus plantarum* LB312R, which is deposited as DSM 33098;

Another aspect of the present invention relates to a composition comprising one or more of the bacterial strains according to the present invention.

Yet another aspect of the present invention relates to a composition according to the present invention for use in treating; alleviating, suppressing; prophylaxis; and/or preventing growth of a pathogenic micro-organism.

DETAILED DESCRIPTION OF THE INVENTION

The present invention relates to probiotic bacteria and a composition for use to prevent or treat infections from pathogenic microorganisms, such as *Staphylococcus* infections. The present invention also relates to composition and to new microbial strains which can inhibit the growth of pathogenic microorganisms, like MRSA.

MRSA may be spread from one subject to another through direct contact with a carrier, e.g. an infected surface or another infected person, such as by sharing personal items that have touched infected skin, or by touching contaminated subjects including skin, nasal passages, animals, surfaces or items.

Despite improvements in treatment, invasive MRSA infections, especially those with an onset in the community or livestock setting, remain problematic and result in a significant financial burden for the healthcare systems in addition to a substantial discomfort to the patient. Similarly, in the European Union, MRSA accounts for 44% of all healthcare-associated infections (HAIs), 22% of attributable extra deaths, and 41% of extra days of hospitalization associated with HAIs. MRSA is a serious public health concern in Japan, which has one of the world's highest crude prevalence rates of MRSA among the various strains of *S. aureus*.

The present invention provides new microbial strains and new composition which can inhibit growth of *Staphylococcus* without contributing to further development of antibiotic resistance.

Thus, a preferred embodiment of the present invention relates to a bacterial strain having a genetic homology of at least 95% to one or more of the bacterial strains selected from the group consisting of:
  *Weissella viridescens* LB10G, which is deposited as DSM 32906;
  *Lactobacillus paracasei* LB113R, which is deposited as DSM 32907;
  *Lactobacillus plantarum* LB244R, which is deposited as DSM 32996;
  *Lactobacillus paracasei* LB116R, which is deposited as DSM 32908;
  *Enterococcus faecium* LB276R, which is deposited as DSM 32997;
  *Lactobacillus plantarum* LB316R, which is deposited as DSM 33091;

*Leuconostoc* mesenteriodes LB341R;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

Thus, another preferred embodiment of the present invention relates to a bacterial strain having a genetic homology of at least 95% to one or more of the bacterial strains selected from the group consisting of:
*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

In the present context the term "genetic homology" relates to a deviation in the genetic sequence of the bacterial strain relative to the deposited bacterial strains. In an embodiment of the present invention the genetic homology may be at least 96%; such as at least 97%; e.g. at least 98%; such as at least 99%; e.g. at least 99.5%; such as at least 99.8%; e.g. at least 99.9%; such as 100% (identical) to one of the bacterial strains selected from the group consisting of:
*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc* mesenteriodes LB341R;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

In another embodiment of the present invention the genetic homology may be at least 96%; such as at least 97%; e.g. at least 98%; such as at least 99%; e.g. at least 99.5%; such as at least 99.8%; e.g. at least 99.9%; such as 100% (identical) to one of the bacterial strains selected from the group consisting of:
*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

In a further embodiment of the present invention the bacterial strain may be selected from the group consisting of:
*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc* mesenteriodes LB341R;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

In an even further embodiment of the present invention the bacterial strain may be selected from the group consisting of:
*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

The effect of the bacterial strain (and/or the composition) according to the present invention on the pathogenic microorganism is significant.

In an embodiment of the present invention the growth of *Staphylococcus aureus*, such as methicillin resistant *Staphylococcus aureus* (MRSA), in co-culture may be reduced by at least 20%; such as reduced by at least 30%, e.g. reduced by at least 40%; such as reduced by at least 50%, e.g. reduced by at least 60%.

In a preferred embodiment the bacterial strain according to the present invention may be an isolated bacterial strain.

The present invention discloses microorganisms which are associated through the functional relationship with one another to form a uniform idea according to the invention, such that they share the properties and/or effects, namely that they inhibit growth of pathogenic microorganisms, like *Staphylococcus aureus*, and/or reduce the colonization level of pathogenic microorganisms, like *Staphylococcus*, associated with skin diseases.

These lactic acid bacteria include in particular microorganisms or analogs, fragments, lysates, derivatives, mutants or combinations thereof selected from the group comprising the following new isolated microorganisms deposited with the German Collection for Microorganisms and Cell Cultures:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc* mesenteriodes LB349R, which is deposited as DSM 33093;
*Lactobacillus plantarum* LB356R, which is deposited as DSM 33094;
*Lactobacillus plantarum* LB312R, which is deposited as DSM 33098;

The present invention encompasses a composition comprising at least one of these new lactic acid bacteria and a composition comprising any combination of these strains and analogs, fragments, lysates, derivatives, mutants hereof.

The inventors of the present invention provides a therapeutic composition for the treatment or prevention of an infection, comprising a therapeutically-effective concentration of one or more species or strains within a pharmaceutically-acceptable carrier suitable for administration to the gastrointestinal tract of a mammal and/or a topical administration on the skin or mucous membranes of a mammal, wherein said probiotic strain possesses the ability to inhibit growth of pathogens, colonization rate and initial attachment of the pathogen to the infection site.

Hence, a preferred embodiment of the present invention relates to a composition comprising one or more of the bacterial strains according to the present invention.

The concentration of the bacterial strain, preferably the one or more viable strain and/or the one or more dead strain, may be in the range of $10^3$ to $10^{14}$ colony forming units (CFU); such as in the range of $10^5$-$10^{13}$ CFU; e.g. in the range of $10^7$-$10^{12}$ CFU; such as in the range of $10^9$-$10^{11}$ CFU.

The concentration of the bacterial strain, preferably one or more dead/inactivated strains, one or more strain lysate; one or more strain metabolites may be in a concentration of 0.001% (w/w) to 20% (w/w).

In the context of the present invention the bacterial strains defined herein may be provided in the composition according to the present invention in the form of a dead bacterial strain. The dead bacterial strain may be provided as whole dead cells or as lysates, metabolites, derivatives, analogs, fractions or extracts obtained from the dead cell.

In a further embodiment of the present invention the one or more of the bacterial strains may be provided as one or more viable strains, one or more dead or inactivated strains, one or more strain lysate; one or more strain metabolites or a combination hereof.

In the composition the bacterial strain according to the present invention may be provided as one or more viable strains, one or more dead or inactivated strains, one or more strain lysate; one or more strain metabolites; one or more analog, one or more fragment, one or more derivative, one or more mutant or combination thereof, where the lysate; one or more strain metabolites; one or more analog, one or more fragment, one or more derivative, one or more mutant or combination thereof (as obtained from the bacterial strains according to the present invention) may treat; alleviate; suppress; prophylaxis; and/or prevent growth of at least one pathogenic microorganism, e.g. MRSA.

In an embodiment of the present invention wherein the composition may be a topical composition, an oral composition or a rectal composition, preferably the composition is a topical composition.

The composition according to the present invention may preferably comprise a pharmaceutically or cosmetically acceptable vehicle or excipient. In an embodiment of the present invention the composition may be provided in solid form, liquid form, viscous form, emulsion or as a dried form.

The composition for oral consumption may preferably be formulated into a paste, a soft gelatin capsule, a hard gelatin capsule, a powder, a talc, a granule, a bead, a pastille, an effervescent tablet, lozenges, buccal tablets, chewable tablets, sublingual tablets, an oil, a liquid, a solution, a tincture, an emulsion, a juice, a concentrate, a syrup, a spray, a mist, a drinking ampoule, a gel, a gum, a tablet, a coated pill or as a food or a feed product or a drink.

In an embodiment of the present invention the composition may be a topical composition for skin of either humans or animals. The composition for topical application may preferably be formulated into a paste; a talc; a lotion; a custard; a foam; a créme; or an ointment.

In an embodiment of the present invention the topical composition may be a powder composition comprising hydrated magnesium silicate (talc) and at least one of the bacterial strains of the invention.

In further embodiment according to the present invention the powder composition for topical application comprises hydrated magnesium silicate, at least one carbohydrate, and at least one of the bacterial strains of the invention.

In a preferred embodiment the topical composition may be formulated into a lotion; a custard; a foam; a créme; or an ointment, oil or emulsion.

In a preferred embodiment the treatment is a combined treatment of both a topical composition and an oral composition comprising the bacterial strains according to the present invention.

The composition may, in addition to the bacterial strains according to the present invention, further comprise other probiotics, prebiotics, antimicrobials, antibiotics or other active antibacterial substances and/or may preferably also contain one or more of the following substances selected from antioxidants, vitamins, coenzymes, fatty acids, amino acids and cofactors.

In another embodiment of the present invention, the bacterial strains according to the present invention may be combined with:

a therapeutically-effective dose of an antibiotic. Either as a co-treatment or following an antibiotic therapy;

a therapeutic concentration of antibiotic including, but not limited to: Fusidic acid; Vancomycin; Gentamicin; Oxacillin; Tetracyclines; Nitroflurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like);

a therapeutically-effective dose of an anti-inflammatory drug. Either as a co-treatment or following a therapy; and/or a therapeutic concentration of anti-inflammatory drug.

In an embodiment of the present invention the composition may be a pharmaceutical, veterinary or food product or a food supplement or a food supplement composition. The composition (preferably for oral administration) may preferably contains one or more thickeners, and/or one or more sweeteners and/or one or more artificial sweeteners, wherein the thickener is preferably selected from cellulose ether, polysaccharides, selected from the group comprising xanthan gum, gelatin, highly dispersed silicon dioxide, starch, carrageenans, alginates, tragacanth, agar, gum arabic, pectin and polyvinyl esters, and the sweetener is selected from the group comprising glucose, fructose, sucrose, glucose syrup, sorbitol, mannitol, xylitol, maltitol, stevia, saccharine, sodium cyclamate, acesulfame K and/or aspartame.

Preferred foods and nutritional supplements in the sense of the invention may comprise effervescent tablets, vitamin tablets, dietary supplements, mineral tablets, trace element tablets, beverage powders, beverages, juices, milk beverages, yogurts, mineral water, uncarbonated water, bonbons, chewable tablets, juice or syrup, coated pills and pastilles as well as aerosols.

Furthermore, the composition may also contain builders, enzymes, electrolytes, pH regulators, thickeners, prebiotics, optical brighteners, graying inhibits, dye transfer inhibitors, foam regulators and/or coloring agents.

Nowhere in the prior art has there been disclosed the use of probiotic strains to prevent or treat infections of pathogenic bacterial infection, like *Staphylococcus* supp., e.g. MRSA, in skin diseases.

It was completely surprising that a group of lactic acid bacteria could be identified that had identical advantageous properties. No bacteria, in particular no lactic acid bacteria combine these properties of treating; alleviating, suppressing; prophylaxis; and/or preventing growth of a pathogenic micro-organism while also being non-pathogenic and not causing any damage to or influence on the skin or to the microbiota.

It will be understood that in the following, preferred embodiments referred to in relation to one broad aspect of the invention are equally applicable to each of the other broad aspects of the present invention described above. It will be further understood that, unless the context dictates otherwise, the preferred embodiments described below may be combined. When used herein, the term topical includes references to formulations that are adapted for application to body surfaces (e.g. the skin or mucous membranes). Mucous membranes that may be mentioned in this respect include the mucosa of the vagina, the penis, the urethra, the bladder, the anus, the mouth (including the mucosa of the cheek, the soft palate, the under surface of tongue and the floor of the mouth), the nose, the throat (including the mucosa of the pharynx, the larynx, the trachea and the esophagus), the bronchi, the lungs, the eye and the ear.

An embodiment of the present invention relates to a composition according to the present invention for use in treating; alleviating, suppressing; prophylaxis; and/or preventing growth of a pathogenic micro-organism.

More preferably the present invention may provide a composition a defined herein for use in the treatment, alleviating, suppressing; prophylaxis of one or more pathogenic bacterial infection in a mammal.

More preferably the present invention may provide a composition a defined herein for use in the preventing growth of a pathogenic micro-organism.

The bacterial infection may preferably be a *Staphylococcus* infection in a mammal. The *Staphylococcus* infection may preferably be an MRSA-infection.

An embodiment of the present invention relates to a composition as defined herein for use in the treatment; alleviation; suppression; and/or the prophylaxis of diseases resulting from *Staphylococcus* infections, such as dermatitis, atopic dermatitis, eczema, carbuncle, cellulitis, rosacea, psoriasis, diaper rash, impetigo or wounds.

In a further embodiment of the present invention the composition comprising at least one of the bacterial strains (or lysates, metabolites, derivatives, analogs, fractions or extracts thereof) to treat skin infections caused by *Staphylococcus aureus* including skin infections associated with atopic dermatitis, eczema, impetigo, burns, or diaper rash.

Burn patients usually are given antibiotics to reduce the incidence of opportunistic infection. *Staphylococcus* spp. are frequently associated with infections of severe burns. Hence, salves, lotions, talc, gels and the like may be combined with the beneficial composition or lysates, metabolites, derivatives, analogs, fractions or extracts obtained from the bacterial strains of the present invention, may be effective in achieving an inhibition of the skin pathogens and preventing growth of the pathogens on the skin of a patient.

Another example is the use of antibiotics in livestock, compositions as disclosed in the present invention may be administrated to the skin or mucous membranes of mammals to reduce colonization of pathogens.

An embodiment of the preferred invention relates to a composition for use as a prophylaxis or medical treatment of *Staphylococcus* infections.

The microorganisms may advantageously be present in viable or killed/dead form in the composition. The bacterial strain may be provided in an encapsulated, micro-encapsulated, spray-dried and/or lyophilized form. Furthermore, the bacterial strain may be provided in the form of a cell lysate, metabolites, derivatives, analogs, fractions or extracts.

In an embodiment of the present invention the bacterial strain may be present in the composition in an amount by weight of 0.001 wt % to 20 wt %, preferably 0.005 wt % to 10 wt %, especially preferably 0.01 wt % to 5 wt %.

A preferred embodiment of the present invention involves the administration of from approximately $1\times10^3$ to $1\times10^{14}$ CFU of viable bacteria per day, more preferably from approximately $1\times10^4$ to $1\times10^{10}$, and most preferably from approximately $5\times10^4$ to $1\times10^9$ CFU of viable bacteria per day. Where the condition to be treated involves antibiotic resistant pathogens and the patient is an adult, the typical dosage is approximately $1\times10^2$ to $1\times10^{14}$ CFU of viable bacteria per day, preferably from approximately $1\times10^8$ to $1\times10^{10}$, and more preferably from approximately $2.5\times10^{8}$ to $1\times10^{10}$ CFU of viable bacteria per day. Where the subject to be treated is an infant over 6 months old, the dosage is typically $1\times10^{6}$ to $1\times10^{9}$ CFU of viable bacteria per day.

Further aspect of the invention the antibiotic resistant bacteria is resistant to at least one of the following antibiotics; fusidic acid, Vancomycin, metronidazole, methicillin and/or fidaxomicin.

The present invention relates to novel bacterial strains and the general reference in the claims relates to viable cells, dead/killed cells and lysates, metabolites, derivatives, analogs, fractions or extracts thereof as well as compositions comprising such viable cells, dead/killed cells and lysates, metabolites, derivatives, analogs, fractions or extracts thereof.

The composition according to the present invention may be suitable for the treating; alleviating, suppressing; prophylaxis; and/or preventing growth of a pathogenic microorganism, such as MRSA, in infants, toddlers, children, healthy persons, the elderly, immunosuppressed people, people with single-occurrence or recurring *Staphylococcus aureus* infections and/or people with antibiotic resistant bacterial infections.

In an embodiment of the present invention the composition according to the present invention may be suitable for the treating; alleviating, suppressing; prophylaxis; and/or preventing growth of a pathogenic micro-organism, such as MRSA, in animals including pets and livestock.

Accordingly, the composition of the present invention may be used to prepare a pharmaceutical drug that is beneficial for the treatment or prevention of growth of *Staphylococcus*. In an embodiment of the present invention the composition may be used curatively or prophylactically, for example, in combination with a probiotic and/or a prebiotic composition.

The combination of the composition according to the present invention and a probiotic strain provides a combined composition capable of inhibiting the growth of *Staphylococcus aureus* in co-culture by reducing the growth of *Staphylococcus aureus* with at least 50% as compared to the growth without the bacterial strain. Wherein growth is measured as colony forming units in stationary growth phase of *Staphylococcus aureus*.

In an embodiment of the present invention the bacterial strain as defined herein may be the only bacteria present in the composition. The composition only comprising bacterial strains as defined herein show reduction in the growth of *Staphylococcus aureus* with at least 50% as compared to the growth without the bacterial strain A "decrease" in growth may be "statistically significant" as compared to the growth period in the absence of the bacterial strains of the present invention, and may include a 1 percent, 2 percent, 3 percent, 4 percent, 5 percent, 6 percent, 7 percent, 8 percent, 9 percent, 10 percent, 11 percent, 12 percent, 13 percent, 14 percent, 15 percent, 16 percent, 17 percent, 18 percent, 19 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, or 100 percent decrease.

In an embodiment of the present invention the growth inhibition may be determined as a decrease in growth of at least 25 percent. Preferably the growth inhibition is determined as a decrease in growth of at least 50 percent. Even more preferably the growth inhibition is determined as a decrease in growth of at least 90 percent.

A "decrease" in the number of microorganisms may be "statistically significant" as compared to the number of CFU/ml in the absence of the bacterial strains of the present invention, and may include a 10 percent, 15 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, 97 percent, 99 percent, 99.9 percent or 100 percent decrease The number of microorganisms is measured as Colony Forming Units CFU/ml.

The microorganisms according to the present invention may preferably by in isolated or purified form, where the term "isolated" means in particular that the lactic acid bacteria are derived from their culture medium including their natural medium, for example. The term "purified" is not restricted to absolute purity.

In an embodiment of the present invention the probiotic strain may be used as a live isolated microorganism in a stabilized form. Suitable methods for stabilization are known to those skilled in the art and includes freeze drying or lyophilization involving different cryoprotectants.

In a further embodiment of the present invention the strain may be used as a live isolated strain.

Preferably, the strain may be used as a live isolated stabilized strain. Even more preferably, the strain may be used as a live isolated strain stabilized by lyophilization. Even more preferably, the strain may be used as a live isolated strain stabilized by lyophilization and comprising a cryoprotectant.

The present invention relates to bacterial strains that are viable and/or are dead (killed), both forms may be included within the scope of the present invention.

Suitable methods for killing (e.g., biological, chemical or physical killing methods) are sufficiently familiar to those skilled in the art. In the present case, however, the bacterial strains may also be used in lyophilized form. The killed forms of the microorganisms can include the fermentation broth and any present metabolites.

The terms "killed" or "dead" relates to inactivated lactic acid bacteria incapable of cell division and without any metabolic activity. Dead or killed lactic acid bacteria may have intact or ruptured cell membranes.

"Lysates", "derivatives", "analogs", "fractions" or "extracts" may be obtained from dead or killed lactic acid bacteria. These lysates, fractions, derivative, analogs, and extracts preferably have the properties of decreasing the transfer of a pathogenic microorganism between a surface of a first subject and a surface of a second subject, where "lysate" as well as the term "extract" refers in particular to a solution or suspension in an aqueous medium of the cells of the microorganism according to the invention and comprises, for example, macromolecules such as DNA, RNA, proteins, peptides, lipids, carbohydrates, etc. as well as cell detritus. The lysate preferably includes the cell wall or cell wall constituents including binding receptors. Methods of producing lysates are sufficiently well known to those skilled in the art and includes, for example, the use of a "French press" or enzymatic lysis, a ball mill with glass beads or iron beads. Cells can be broken open by enzymatic, physical or chemical methods. Examples of enzymatic cell lysis may include individual enzymes as well as enzyme cocktails, for example, proteases, proteinase K, lipases, glycosidases; chemical lysis may be induced by ionophores, detergents such as SDS, acids or bases; physical methods may also be implemented by using high pressures such as the French press, osmolarities, temperatures or alternating between heat and cold. Furthermore chemical, physical and enzymatic methods may of course be combined.

In a preferred embodiment the composition and/or the bacterial strains according to the present invention is suitable for treating; alleviating, suppressing; prophylaxis a disease associated with a pathogenic microorganism infection in a mammal.

In an embodiment the disease may be selected from the group of skin diseases being sensitive to Staphylococcal infections comprising psoriasis, atopic dermatitis, carbuncle, cellulitis, rosacea, psoriasis, dry skin, allergy, eczema, rashes, UV-irritated skin, detergent irritated skin (including irritation caused by enzymes used in washing detergents and sodium lauryl sulphate), thinning skin (e.g. skin from the elderly and children).

The present invention also relates to a method to decrease number of *Staphylococcus* on the skin of a patient with atopic dermatitis.

In an embodiment of the invention, the composition comprising at least one bacterial strain may be used to control the number of *Staphylococcus aureus* on the skin of patients with inflammatory skin diseases at a level where the *Staphylococcus* does not result in an infection of the skin.

In yet an embodiment of the invention, the composition comprising at least one bacterial strain may be used to control the number of *Staphylococcus aureus* on the skin of patients with inflammatory skin diseases wherein the level of *Staphylococcus aureus* is below approximately $10^5$ CFU/$cm^3$ of the skin.

It will be clear to those skilled in the art that here, as well as in all the statements of range given in the present invention, characterized by such terms as "about" or "approximately," that the precise numerical range need not be indicated with expressions such as "about" or "approx." or "approximately," but instead even minor deviations up or down with regard to the number indicated are still within the scope of the present invention. In an embodiment of the present invention, the minor deviation may include a 5% deviation or less, such as a 4% deviation or less, e.g. a 3% deviation or less, such as a 2% deviation or less, e.g. a 1% deviation or less.

In an embodiment of the present invention, a biologically pure culture of one or more of the bacterial strain(s) of the present invention may be provided.

In the present context the term "mammal" may include humans, primates, farm animals, sport animals, rodents and pets. Non-limiting examples of non-human animal subjects include rodents such as mice, rats, hamsters, and guinea pigs; rabbits; dogs; cats; sheep; pigs; piglets; sows; poultry; turkeys; broilers; minks; goats; cattle; horses; and non-human primates such as apes and monkeys.

The term "effective amount" may depends upon the context in which it is being applied. In the context of administering a composition to reduce the risk of *Staphylococcus* infection, and/or administering a composition to reduce the severity of *Staphylococcus* infection and/or decreasing the amount of *Staphylococcus aureus* in a subject, an effective amount of a composition described herein is an amount sufficient to treat and/or ameliorate an *Staphylococcus* infection, as well as decrease the severity and/or reduce the likelihood of a *Staphylococcus* infection and/or the transfer of *Staphylococcus* between subjects. The decrease in the amount of *Staphylococcus aureus* in a subject, may be a 10 percent decrease, 20 percent decrease, 30 percent decrease, 40 percent decrease, 50 percent decrease, 60 percent decrease, 70 percent decrease, 80 percent decrease, 90 percent decrease, 95 percent decrease, 98 percent decrease, 99 percent decrease or 99.9 percent decrease in severity of *Staphylococcus* infection, or likelihood of becoming infected.

An effective amount may be administered as a composition in one or more administrations.

The effective amount of the composition can be administered as a topical administration, an oral administration or a combination thereof. Preferably as a topical administration.

The composition may be applied in more than one type of administration, such as into the feed or food for a mammal and/or applied to the skin and/or applied as a nasal application.

In an embodiment of the present invention the composition comprising the at least one bacterial strain according to the present invention and a prebiotic.

"Prebiotics" are non-digestible food components that increase the growth of specific microorganisms. "Synbiotics" are compositions comprising at least one probiotic and at least one prebiotic. Such compositions are understood to encourage the growth of beneficial bacteria (e.g. the probiotic). Thus, powerful synbiotics are based on a combination of specific strains of probiotic bacteria with carefully selected prebiotics. They can lead to an important health benefit to a mammal.

According to another aspect of the present invention there is provided a probiotic composition comprising the probiotic microorganism and at least one more active ingredient.

Prebiotics refer to chemical products that induce the growth and/or activity of commensal microorganisms (e.g., bacteria and fungi) that contribute to the well-being of their host. Prebiotics are nondigestible carbohydrates that pass undigested through the upper part of the gastrointestinal tract and stimulate the growth and/or activity of advantageous bacteria that colonize the large bowel or skin microorganisms.

Some oligosaccharides that are used as prebiotics are fructooligosaccharides (FOS), xylooligosaccharides (XOS), polydextrose, pectins, galactooligosaccharides (GOS) or human milk oligo saccharides (HMO). Moreover disaccharides like lactulose or some monosaccharides such as lactose or tagatose can also be used as prebiotics.

In an embodiment of the present invention at least one prebiotic compound may be comprised in the composition of the invention. In a very broad concept, prebiotics are all those compounds which can be metabolized by probiotics.

Preferably prebiotics are non-digestible or poorly digestible by a mammal. Thus, following uptake by the mammal, the non-digestible prebiotics can pass through the small intestine and enter the large intestine to stimulate the growth of the probiotics in this compartment. Prebiotics can thus serve as a food source for probiotics. It is believed that the prebiotics, many of which are non-digestible carbohydrates, promote the growth of probiotics. Prebiotics are naturally found for example in cabbage, onions, whole grains, bananas, garlic, honey, leeks, artichokes, fortified foods and beverages, as well as dietary supplements. Prebiotics are well known in the art and when used in the present invention there is no particular limitation of the prebiotic as such.

In an embodiment however the at least one prebiotic product in the composition is selected from the following compounds and compositions: non-digestible carbohydrates, beta-glucans, mannan-oligosaccharides, inulin, oligofructose, human milk oligosaccharides (HMO), galactooligosaccharides (GOS), lactulose, lactosucrose, galactotriose, fructo-oligosaccharide (FOS), cellobiose, cellodextrins, cylodextrins, maltitol, lactitol, glycosilsucrose, betaine, Vitamin E or a variant thereof (wherein the variants are selected from alfa, beta, gamma, delta tocoferols, tocotrienols and tocomonoenols). Optionally, mannan-oligosaccharides and/or inulin may be preferred. HMOs may include lacto-N-tetraose, lacto-N-fucopentaose, lacto-N-triose, 3'-sialyllactose, lacto-N-neofucopentaose, sialic acid, L-fucose, 2-fucosyllactose, 6'-sialyllactose, lacto-N-neotetraose and 3-fucosyllactose.

Prebiotics may also be used in topical compositions of the invention.

In an embodiment at least one of the following prebiotic compounds are used in the topical composition of the invention; lactose, beta-glucans, mannan-oligosaccharides, inulin, oligofructose, galactooligosaccharides (GOS), lactulose, lactosucrose, galactotriose, fructo-oligosaccaride (FOS), cellobiose, cellodextrins, cylodextrins, maltitol, lactitol, glycosilsucrose, betaine, Vitamin E or a variant thereof (wherein the variants are selected from alfa, beta, gamma, delta tocoferols, tocotrienols and tocomonoenols), lacto-N-tetraose, lacto-N-fucopentaose, lacto-N-triose, 3'-sialyllactose, lacto-N-neofucopentaose, sialic acid, 2-fucosyllactose, 6'-sialyllactose, lacto-N-neotetraose and 3-fucosyllactose. Optionally, lactose and/or mannan-oligosaccharides and/or inulin may be preferred.

D- and L-fucose strengthen natural defense of skin, stimulate epidermis immune defense and/or prevent and/or treat cutaneous autoimmune disease. In an embodiment of the invention the composition comprises D- or L-fucose.

In an embodiment of the invention the composition further comprises L-fucose in a concentration in the composition of 10 mM to 500 mM.

According to still further features in the described preferred embodiments the composition further comprises at least one active ingredient.

In an embodiment of the present invention the composition comprising at least on bacterial strain of the invention in combination with at least one further probiotic microorganism selected from the group consisting of another bacteria, a yeast or a mold.

The composition according to the present invention may comprise at least one bacterial strain in combination with at least one further probiotic microorganism, wherein the at least one further probiotic microorganism may be selected from but not restricted to: *Bifidobacterium lactis* DSM10140, *B. lactis* LKM512, *B. lactis* DSM 20451, *Bifidobacterium bifidum* BB-225, *Bifidobacterium adolescentis* BB-102, *Bifidobacterium breve* BB-308, *Bifidobacterium longum* BB-536 from Zaidanhojin Nihon Bifizusukin Senta (Japan *Bifidus* Bacteria Center), *Bifidobacterium* NCIMB 41675 described in EP2823822. *Bifidobacterium bifidum* BB-225, *Bifidobacterium adolescentis* BB-102, *Bifidobacterium breve* BB-308, *Bifidobacterium lactis* HN019 (Howaru) available from DuPont Nutrition Biosciences ApS, *Bifidobacterium lactis* DN 173 010 available from Groupe Danone, *Bifidobacterium lactis* Bb-12 available from Chr. Hansen A/S, *Bifidobacterium lactis* 420 available from DuPont Nutrition Biosciences ApS, *Bifidobacterium breve* Bb-03, *B. lactis* BI-04, *B. lactis* Bi-07 available from DuPont Nutrition Biosciences ApS, *Bifidobacterium bifidum* Bb-02, *Bifidobacterium bifidum* Bb-06, *Bifidobacterium longum* KC-1 and *Bifidobacterium longum* 913 (DuPont Nutrition Biosciences ApS), *Bifidobacterium breve* M-16V (Morinaga) and/or a *Lactobacillus* having a probiotic effect and may be any of the following strains; *Lactobacillus rhamnosus* LGG (Chr. Hansen), *Lactobacillus acidophilus* NCFM (DuPont Nutrition Biosciences ApS), *Lactobacillus bulgaricus* 1260 (DuPont Nutrition Biosciences ApS), *Lactobacillus paracasei* Lpc-37 (DuPont Nutrition Biosciences ApS), *Lactobacillus rhamnosus* HN001 (Howaru) available from DuPont Nutrition Biosciences ApS, *Streptococcus thermophilus* 715 and *Streptococcus thermophilus* ST21 available from DuPont Nutrition Biosciences ApS, *Lactobacillus paracasei* subsp. *paracasei* CRL431 (ATCC 55544), *Lactobacillus paracasei* strain F-19 from Medipharm, Inc. *L. paracasei* LAFTI L26 (DSM Food Specialties, the Netherlands) and *L. paracasei* CRL 431 (Chr. Hansen), *Lactobacillus acidophilus* PTA-4797, *L. salivarius* Ls-33 and *L. curvatus* 853 (DuPont Nutrition Biosciences ApS). *Lactobacillus casei* ssp. *rhamnosus* LC705 is described in FI Patent 92498, Valio Oy, *Lactobacillus* DSM15527 (Bifodan), *Lactobacillus* DSM15526 (Bifodan), *Lactobacillus rhamnosus* GG (LGG) (ATCC 53103) is described in U.S. Pat. No. 5,032,399 and *Lactobacillus rhamnosus* LC705 (DSM 7061), Propionic acid bacterium eg. *Propionibacterium freudenreichii* ssp. *shermanii* PJS (DSM 7067) described in greater details in FI Patent 92498, Valio Oy, *Nitrosomonas eutropha* D23 (ABIome), *Staphylococcus hominis* strains A9, C2, AMT2, AMT3, AMT4-C2, AMT4-GI, and/or AMT4-D12. (all from Matrisys Bioscience), *Staphylococcus epidermidis* strains M034, M038, All, AMT1, AMT5-C5, and/or AMT5-G6 (all from Matrisys Bioscience), *L. plantarum* YUN-V2.0 (BCCM LMG P-29456), *L. pentosus* YUN-V1.0 (BCCN LMG P-29455), *L. rhamnosus* YUN-S1.0 (BCCM LMG P-2961) and/or any combinations hereof.

In an embodiment of the present invention the composition comprises at least one bacterial strain as defined herein in combination with at least one strain selected from the group of lactic acid bacteria being able to improve tight junction integrity.

In a further embodiment of the present invention the composition comprises at least one bacterial strain as defined herein in combination with at least one strain selected from the group of *Lactobacillus rhamnosus* LGG (Chr. Hansen), *Lactobacillus acidophilus* NCFM (DuPont), *Lactobacillus salivarius* Ls-33 (DuPont), *Propionibacterium jensenii* P63 (DuPont), *Bifidobacterium lactis* 420 (DuPont) and *L. acidophilus* La-14 (DuPont); and/or the cell lysate and/or the soluble metabolite of the probiotic strain.

The composition according to the present invention suitable for oral consumption may be provided with from $1\times10^6$ to $1\times10^{14}$ Colony Forming Units (CFU) per serving, or per dose.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of disease, stabilized (i.e., not worsening) state of disease, prevention of disease, delay or slowing of disease progression, and/or amelioration or palliation of the disease state. The decrease can be a 10 percent, 20 percent, 30 percent, 40 percent, 50 percent, 60 percent, 70 percent, 80 percent, 90 percent, 95 percent, 98 percent or 99 percent decrease in severity of complications or symptoms.

In an embodiment of the present invention a method of treating the skin of mammals may be provided. The method comprising administering to a subject (e.g. a mammal) in need thereof a therapeutically effective amount of at least one bacterial strain, thereby treating skin to reduce colonization and/or carrier level and/or infection.

In a further embodiment of the present invention the skin colonization may be caused by an antibiotic resistant microorganism. The skin colonization may be caused by MRSA.

The at least one bacterial strain may be capable of proliferating and colonizing in a mammalian gastrointestinal tract, nasal passages or skin.

The present invention may provide several advantages. In particular, insofar as there is a detrimental effect to the use of antibiotics because of the potential to produce antibiotic resistant microbial species, it is desirable to have an antimicrobial treatment which does not utilize conventional antimicrobial agents. Hence, the present invention does not contribute to the production of future generations of antibiotic resistant pathogens.

In an embodiment of the present invention the effect of the composition according to the present invention and the method according to the present invention does not involve a rinsing step for removing the biofilm from the surface before adding the at least one lactic acid bacterium.

Deposit of Biological Material

The following biological material, microorganisms, have been deposited at the with the German Collection for Microorganisms and Cell Cultures:

*Weissella viridescens* LB10G, which is deposited as DSM 32906;

*Lactobacillus paracasei* LB113R, which is deposited as DSM 32907;

*Lactobacillus plantarum* LB244R, which is deposited as DSM 32996, deposited with the Leibniz Institute DSMZ-German Collection of Microorganisms and Cell Cultures ("DSMZ"), currently located at Inhoffstraße 7B, D-38124 Braunschweig, Germany, under the terms of the Budapest Treaty on Dec. 13, 2018;

*Lactobacillus paracasei* LB116R, which is deposited as DSM 32908;

*Enterococcus faecium* LB276R, which is deposited as DSM 32997;

*Lactobacillus plantarum* LB316R, which is deposited as DSM 33091;

*Leuconostoc mesenteriodes* LB349R, which is deposited as DSM 33093;

*Lactobacillus plantarum* LB356R, which is deposited as DSM 33094, deposited with the Leibniz Institute DSMZ-German Collection of Microorganisms and Cell Cultures ("DSMZ"), currently located at Inhoffstraße 7B, D-38124 Braunschweig, Germany, under the terms of the Budapest Treaty on Apr. 10, 2019;

*Lactobacillus plantarum* LB312R, which is deposited as DSM 33098;

It should be noted that embodiments and features described in the context of one of the aspects of the present invention also apply to the other aspects of the invention.

The invention will now be described in further details in the following non-limiting examples.

EXAMPLES

Example 1 Strain Screening Identification Samples

For identification and selection of bacterial strain(s) according to the invention, a strain collection of lactic acid bacteria (LAB) was established. Samples from different origins, such as homemade sauerkraut, kimchi and healthy human donor samples (vaginal, oral, anal, skin) were collected for isolation of at least 995 lactic acid bacteria. The samples were collected on Man Rogosa Sharp (MRS, Sigma-Aldrich) broth and agar cultured anaerobically at 37° C. overnight or until colony formation. The isolates are plated and sub-cultured until pure colonies were obtained. The pure colonies are stored in MRS broth with 25% glycerol at −80° C. for future use. Strains were identified using 16S rRNS Sanger sequencing standard methods.

Example 2 Co-Culture Assay/Competition Assay

Competition between bacterial strains and *Staphylococcus aureus* was determined according to the methods described in the following publications: Dowarah, R., et al. 2018, Selection and characterization of probiotic lactic acid bacteria and its impact on growth, nutrient digestibility, health and antioxidant status in weaned piglets. PLoS ONE, 13(3), Khare, A., & Tavazoie, S. (2015). Multifactorial Competition and Resistance in a Two-Species Bacterial System. PLoS Genetics, 11(12), 1-21.)

*Staphylococcus aureus* subsp. *aureus* COL (CCOS461), *Staphylococcus aureus* CC1 (Bispebjerg University Hospital, Clausen et al. (2017) Br. J. Dermatol. 177: 1394-1400. Doi 10.1111/bjd.15470) and *Staphylococcus aureus* US300 (ATCC BAA-1717) were used as test organisms. *S. aureus* were cultured in Brain Heart Infusion (BHI) broth. *S. aureus* CC1 is the clonal type especially related to atopic dermatitis and associated with the FLG mutations patients with atopic dermatitis.

The cell density of overnight culture of *S. aureus* and bacterial strain isolates was adjusted according to an optical density at 600 nm (OD600) of 1 and harvested by centrifugation (6.000 rpm for two minutes). The cell pellet is washed twice in phosphate buffered saline (1×PBS) and resuspended in 1×PBS. One milliliter of each cell suspensions is mixed in 50 mL of BHI broth and co-incubated at 37° C. for 24 hours, while monocultures of each *Staphylococcus aureus* and each LAB are used as controls. At time 0, 2 hours, 6 hours, 10 hours and 24 hours, serial dilutions of the cell solutions are plated out on nutrient agar plates to count forming colonies. MRS agar was used for LAB isolates and Mannitol Salt Phenol Red Agar (Sigma-Aldrich) was used for *Staphylococcus aureus*.

*Lactobacillus rhamnosus* LGG (Chr. Hansen) was used as a control probiotic strain in all experiments. 22 strains of lactic acid bacteria (LAB) from the collection of 675 bacterial strains were identified as being able to out-compete growth of all three tested *Staphylococcus aureus* strains determined as an ability to decrease growth of the test strain with at least 25%. 8 bacterial strains were determined to decrease growth with more than 90%. *L. rhamnosus* LGG was not able to out-compete growth of any *Staphylococcus aureus*.

Example 3 Co-Aggregation

Co-aggregation was determined according to known methods Cisar, J. O. et al. (1979). "Specificity of Coaggregation Reactions between Human Oral Streptococci and Strains of *Actinomyces Viscosus* or *Actinomyces Naeslundii*." Infection and Immunity 24 (3): 742-52. Inoculum of all bacterial strains was grown in MRS broth and the *S. aureus* strains was grown in BHI broth overnight at 37° C. Overnight cell samples are harvested by centrifugation (6000 rpm for 2 min), and supernatant was removed from the pellet. The pellet is washed twice in 1×PBS buffer.

Cell pellet was resuspended in 1×PBS and 500 µl of *S. aureus* and bacterial strains were aliquoted into 24 well plates. The plates were incubated on a shaker (200 rpm).

Auto- and co-aggregation formation is observed visually after 1 hour, 2 hours, 3 hours and 24 hours.

As a control for self-aggregation, samples of *S. aureus* and bacterial strains were mixed with PBS buffer 750 µl of buffer resulting in a final volume of 1500 µl in each well.

The plates were incubated on a shaker at approximately 200 rpm for 24 hours. Co-aggregation formation is observed after 1 hour, 2 hours, 3 hours and 24 hours.

The formation of co-aggregation was scored visually from 1-5 using the following scale:
1: No aggregation
2: Visual initial aggregation
3: Formation of aggregates <0.5 mm
4: Formation of aggregates >0.5 mm and <1 mm
5: Formation of aggregates >1 mm

TABLE 1

Co-aggregation measured using a visual evaluation from 1 to 5 (see scale above). Data shown for 1 hour and 24 hours incubation

| LAB | S. aureus COL | | S. aureus CC1 | | S. aureus US300 | |
|---|---|---|---|---|---|---|
| | 1 h | 24 h | 1 h | 24 h | 1 h | 24 h |
| *Weissella viridescens* LB10G | 2 | 3 | 2 | 3 | 2 | 3 |
| *Lactobacillus paracasei* LB113R | 4 | 5 | 2 | 3 | 3 | 5 |
| *Lactobacillus plantarum* LB244R | 2 | 3 | 2 | 3 | 3 | 3 |
| *Lactobacillus paracasei* LB116R | 3 | 4 | 3 | 4 | 3 | 4 |
| *Enterococcus faecium* LB276R | 2 | 3 | 2 | 3 | 2 | 2 |
| *Lactobacillus plantarum* LB312R | 4 | 5 | 4 | 4 | 4 | 4 |
| *Lactobacillus plantarum* LB316R | 3 | 5 | 4 | 4 | 3 | 5 |
| *Leuconostoc mesenteroides* LB341R | 3 | 4 | 5 | 4 | 5 | 5 |
| *Leuconostoc mesenteroides* LB349R | 3 | 3 | 3 | 3 | 2 | 3 |
| *Lactobacillus plantarum* LB356R | 4 | 5 | 4 | 4 | 4 | 4 |
| *Lactobacillus rhamnosus* LGG | 1 | 1 | 1 | 1 | 1 | 1 |

Example 4 Spot on Lawn Assay

Spot on lawn test for growth inhibition and antimicrobial metabolites were tested using the methods described in Zhang P. et al.(2015) Interstrain interactions between bacteria isolated from vacuum-packaged refrigerated beef. Appl Environ Microbiol 81:2753-2761. doi:10.1128/AEM.03933-14 and Arena, M. P. et al.(2016) Use of *Lactobacillus plantarum* Strains as a Bio-Control Strategy against Food-Borne Pathogenic Microorganisms. Frontiers in Microbiology 7 (APR): 1-10. https://doi.org/10.3389/fmicb.2016.00464.

Bacterial strain isolates from example 1 were cultured from storage samples into 2 mL of MRS broth in 24-well plates. *S. aureus* test strains were cultured in approximately 200 mL of BHI broth in Erlenmeyer flask. The LAB isolates and *S. aureus* solutions were grown overnight at 37° C. The cell density of the overnight culture of *S. aureus* is adjusted in BHI broth to an optical density at 600 nm (OD600) of 1 and hereafter diluted in PBS buffer to a 10^-2 dilution. Two hundred microliters of cell suspension were spread onto BHI agar plates. The plates with *S. aureus* lawn were left for drying for appr. 10-20 minutes in sterile air. Three replicates of 20 µL of isolated LAB was spotted onto the *S. aureus* lawn. The plates were left for drying and hereafter incubated at 37° C. aerobically overnight. The plates are photographed, and the inhibition zone is measured in mm as the clearing zone around the spot. Growth inhibition is observed as the bacterial strain being able to overgrow the *Staphylococcus* strain in the spot area indicated in table 2 as a (+). If the *Staphylococcus* strain is able to outgrow the spotted bacterial strain, then there is no detected grow inhibition indicated in table 2 as a (−).

5 LAB strains were identified as having a significant growth inhibitory effect on *S. aureus* and also an inhibition zone of more than 1 mm around spot. *L. rhamnosus* LGG (Chr. Hansen) was used as a control commercial probiotic strain. *L. rhamnosus* was not able to growth inhibit any of the *Staphylococcus* test strains nor did *L. rhamnosus* LGG give any clearing zone.

TABLE 2

Growth inhibition and antimicrobial metabolites. Inhibition zone is determined as average of three measurements.

| LAB | Growth inhibition in spot. | | | Inhibition zone: clearing around the spot (mm) | | |
|---|---|---|---|---|---|---|
| | S.a. COL | S.a. CC1 | S.a. US300 | S.a. COL | S.a. CC1 | S.a. US300 |
| *Weissella viridescens* LB10G | + | + | + | 3 | 4 | 4 |
| *Lactobacillus paracasei* LB113R | + | + | + | 2 | 2 | 2 |
| *Lactobacillus plantarum* LB244R | + | + | + | 7 | 11 | 5 |
| *Lactobacillus paracasei* LB116R | + | + | + | 1 | 2 | 1 |
| *Enterococcus faecium* LB276R | + | + | + | 5 | 6 | 4 |
| *Lactobacillus plantarum* LB312R | + | + | + | 9 | 8 | 8 |
| *Lactobacillus plantarum* LB316R | + | + | + | 2 | 3 | 3 |
| *Leuconostoc mesenteroides* LB341R | + | + | + | 2 | 2 | 1 |
| *Leuconostoc mesenteroides* LB349R | + | + | + | 11 | 11 | 10 |
| *Lactobacillus plantarum* LB356R | + | + | + | 8 | 8 | 7 |
| *Lactobacillus rhamnosus* LGG | − | − | − | 0 | 0 | 0 |

A significant inhibition of CC1 was determined, this clonal complex type of *Staphylococcus aureus* is especially associated with *Staphylococcus aureus* infections in atopic dermatitis (Clausen et al. (2017) Br. J. Dermatol. 177: 1394-1400. Doi 10.1111/bjd.15470).

*Lactobacillus acidophilus* NCFM, *Lactobacillus salivarius* Ls-33, *Bifidobacterium lactis* 420, *Lactobacillus acidophilus* La-14 and *Probionibacterium jensenii* P63 (all commercially available from DuPont) are all associated as being able to improve disorders related with tight junction function e.g. atopic dermatitis by improving the barrier function of the skin. However, in spot on lawn test with CC1 none of these commercial probiotic strains are able to growth inhibit CC1 and will thus not be able to prevent or treat a *Staphylococcus* infection.

The invention claimed is:

1. A bacterial strain capable of treating, alleviating, suppressing, prophylaxis, and/or preventing growth of a pathogenic micro-organism wherein the one or more bacterial strain is *Lactobacillus plantarum* LB356R, which is deposited as DSM 33094 or *Lactobacillus plantarum* LB244R, which is deposited as DSM 32996, and wherein the one or more bacterial strains is provided as one or more viable strains, one or more dead or inactivated strains, one or more strain lysate: one or more strain metabolites or a combination hereof, or wherein the viable bacterial strain is provided in an encapsulated, micro-encapsulated, spray-dried and/or lyophilized form.

2. The bacterial strain according to claim 1, wherein the growth of *Staphylococcus aureus* in co-culture is reduced by at least 20%.

3. The bacterial strain according to claim 1, wherein the bacterial strain is an isolated bacterial strain.

4. A composition comprising one or more of the bacterial strains according to claim 1.

5. The composition according to claim 4, wherein the composition is formulated into an emulsion; an oil; a gum; a paste; a powder, a talc; a lotion; a custard; a foam; a créme; a gel; an ointment; a suspension; a mist; or a liquid.

6. The composition according to claim 4, wherein the composition is a topical composition, an oral composition or a rectal composition.

7. The composition according to claim 4, wherein the concentration of the bacterial strain is in the range of $10^3$ to $10^{14}$ colony forming units (CFU).

8. The composition according to claim 4, wherein the concentration of the bacterial strain is in a concentration of 0.001% (w/w) to 20% (w/w).

9. The composition according to claim 4, wherein the composition further comprises a prebiotic composition.

10. The composition according to claim 4, wherein the one or more bacterial strain are the only bacteria present in the composition.

11. The composition according to claim 4, for treating; alleviating, suppressing; prophylaxis; and/or preventing growth of a pathogenic micro-organism.

12. A method for treatment; alleviation; suppression; and/or the prophylaxis of one or more pathogenic bacterial infections or antibiotic resistant bacterial infections in a mammal, comprising administration of the composition according to claim 4.

13. The method according to claim 12, wherein bacterial infection is a *Staphylococcus* infection in a mammal.

14. The method according to claim 13, wherein the *Staphylococcus* infection is an MRSA-infection.

15. The method according to claim 12, for the treatment; alleviation; suppression; and/or the prophylaxis of diseases resulting from *Staphylococcus* infections.

\* \* \* \* \*